US011834695B2

(12) United States Patent
Tsuji et al.

(10) Patent No.: US 11,834,695 B2
(45) Date of Patent: Dec. 5, 2023

(54) MARKER AND METHOD FOR DETERMINATION OF PARKINSON'S DISEASE

(71) Applicants: KABUSHIKI KAISHA YAKULT HONSHA, Minato-ku (JP); NATIONAL UNIVERSITY CORPORATION NAGOYA UNIVERSITY, Nagoya (JP)

(72) Inventors: Hirokazu Tsuji, Minato-ku (JP); Takashi Asahara, Minato-ku (JP); Koji Nomoto, Minato-ku (JP); Masaaki Hirayama, Nagoya (JP); Kinji Ohno, Nagoya (JP)

(73) Assignees: KABUSHIKI KAISHA YAKULT HONSHA, Minato-ku (JP); NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 334 days.

(21) Appl. No.: 16/612,968

(22) PCT Filed: May 17, 2018

(86) PCT No.: PCT/JP2018/019148
§ 371 (c)(1),
(2) Date: Nov. 12, 2019

(87) PCT Pub. No.: WO2018/212288
PCT Pub. Date: Nov. 22, 2018

(65) Prior Publication Data
US 2021/0010052 A1  Jan. 14, 2021

(30) Foreign Application Priority Data
May 18, 2017  (JP) ................. 2017-098973

(51) Int. Cl.
*C12Q 1/06* (2006.01)
*C12Q 1/6851* (2018.01)
*C12Q 1/689* (2018.01)
*C12N 1/20* (2006.01)
*G01N 33/92* (2006.01)
*C12R 1/24* (2006.01)
*C12R 1/25* (2006.01)

(52) U.S. Cl.
CPC ............... *C12Q 1/06* (2013.01); *C12N 1/20* (2013.01); *C12Q 1/689* (2013.01); *G01N 33/92* (2013.01); *C12Q 1/6851* (2013.01); *C12R 2001/24* (2021.05); *C12R 2001/25* (2021.05)

(58) Field of Classification Search
CPC . C12Q 1/06; C12Q 1/689; C12Q 1/10; C12Q 1/6851; C12N 1/20; C12R 2001/24; C12R 2001/25; G01N 2333/24; G01N 2333/335; G01N 2800/2835
See application file for complete search history.

(56) References Cited

U.S. PATENT DOCUMENTS

| 2009/0170078 A1* | 7/2009 | Tsuji ................. C12Q 1/689 435/6.15 |
| 2014/0147856 A1 | 5/2014 | Forsyth et al. |
| 2016/0106789 A1 | 4/2016 | Nofar et al. |

FOREIGN PATENT DOCUMENTS

| CN | 104726596 | 6/2015 | |
| CN | 105063194 | 11/2015 | |
| WO | WO-2015181449 A1 * | 12/2015 | ............... C12Q 1/68 |
| WO | WO 2016/167365 | 10/2016 | |

OTHER PUBLICATIONS

Hasegawa et al. Intestinal Dysbiosis and Lowered Serum Lipopolysaccharide-Binding Protein in Parkinson's Disease. PLoS One. 2015;10(11):e0142164.*
Shigemori et al. RTehseaerc hf aartcictleorial structure of the mini mental state examination (MMSE) in Japanese dementia patients. BMC Geriatrics. 2010;10:36.*
International Search Report dated Aug. 14, 2018 in PCT/JP2018/019148 filed on May 17, 2018.
Hasegawa, S. et al., "Intestinal Dysbiosis and Lowered Serum Lipopolysaccharide-Binding Protein in Parkinson's Disease", PLOS One, 2015, vol. 10, No. 11, retrieved from the Internet (on Aug. 3, 2018): <URL: http://europepmc.org/backend/ptpmcrender.fcgi?accid=PMC4634857&blobtype=pdf>, pp. 1-15.
Saiki, H., "Medical Care for Parkinson's Disease, Questions and Answers", Parkinson's Disease and Unified Parkinson's Disease Rating Scale (UPDRS), Front. Parkinson Dis., 2013, vol. 6, No. 1, pp. 44-48, 7 total pages (with partial English translation).
Hawkes, C. H. et al., "A timeline for Parkinson's disease", Parkinsonism and Related Disorders, 2010, vol. 16, No. 2, pp. 79-84.
Katzenschlager, R. et al., "Olfaction and Parkinson's syndromes: its role in differential diagnosis", Current Opinion in Neurology, 2004, vol. 17, No. 4, pp. 417-423.
Hirayama, M. et al., "A scintigraphical qualitative analysis of peripheral vascular sympathetic function with meta-[$^{123}$I]iodobenzylguanidine in neurological patients with autonomic failure", Journal of the Autonomic Nervous System, 1995, vol. 53, Nos. 2-3, pp. 230-234.

(Continued)

Primary Examiner — Lynn Y Fan
(74) Attorney, Agent, or Firm — Oblon, McClelland, Maier & Neustadt, L.L.P.

(57) ABSTRACT

The present invention relates to a method for simply diagnosing the progress of disease condition of a Parkinson's disease patient. Provided are a method for determining Parkinson's disease using the number of one or more intestinal bacteria selected from the group consisting of *Bifidobacterium*, *Bacteroides fragilis* group, *Lactobacillus brevis*, and *Lactobacillus plantarum* subgroup and/or the total number of intestinal bacteria as a marker, and a method for determining Parkinson's disease using the blood LPS level and/or the blood LBP level of a Parkinson's disease patient as an indicator.

7 Claims, 6 Drawing Sheets
Specification includes a Sequence Listing.

(56) References Cited

OTHER PUBLICATIONS

Abbott, R.D. et al., "Frequency of bowel movements and the future risk of Parkinson's disease", Neurology, 2001, vol. 57, No. 3, pp. 456-462.
European Search Report dated Apr. 1, 2021 in corresponding European Patent Application No. 18802093.7, 18 pages.
Masaaki Hirayama, et al., "Intestinal Dysbiosis and Lowered Serum Lipopolysaccharide-Binding Protein in PD", Parkinsonism & Related Disorders, vol. 22: 2016, DOI:10.1016/j.parkreldis2015.10.034, pp. 1.
Arun Parashar et al., "Gut Microbiota: Implications in Parkinson's Disease", Parkinsonism & Related Disorders, vol. 38, Feb. 7, 2017, pp. 1-7.
Gian D. Pal et al., "Abnormal Lipopolysaccharide Binding Protein as Marker of Gastrointestinal Inflammation in Parkinson Disease", Front. Neurosci., vol. 9, Sep. 1, 2015, pp. 1-5.
Partial Supplementary European Search Report dated Jan. 25, 2021 in corresponding European Patent Application No. 18802093.7, 14 pages.
J. R. Bedarf et al., "Functional implications of microbial and viral gut metagenome changes in early stage L-DOPA-naïve Parkinson's disease patients", Genome Medicine vol. 9, No. 1, Apr. 28, 2017, pp. 1-13.
Ali Keshavarzian et al., "Colonic bacterial composition in Parkinson's disease", Movement Disorders, vol. 30, No. 10, Jul. 16, 2015, pp. 1351-1360.
Tomomi Minato et al., "Progression of Parkinson's disease is associated with gut dysbiosis: Two-year follow-up study", Plos One, vol. 12, No. 11, Nov. 1, 2017, p. e0187307(pp. 1-14).
Combined Russian Office Action and Search Report dated Feb. 24, 2022 in Russian Patent Application No. 2019141648 (with unedited computer generated English transiation), 16 pages.
Matsuda. K.. et al., "Establishment of an Analytical System for the Human Fecal Microbiota, Based on Reverse Transcription-Quantitative PCR Targeting of Multicopy rRNA Molecules", Applied and Environmental Microbiology, Apr. 2009, vol. 75, No. 7, pp. 1961-1969.
Office Action dated Nov. 30, 2022, for Chinese Patent Application No. 201880032872.2 (with machine translation)—12 pages.

* cited by examiner

SEQUENCE LISTING

<160> NUMBER OF SEQ ID NOS: 38

<210> SEQ ID NO 1
<211> LENGTH: 20
<212> TYPE: DNA

```
<213> ORGANISM: Artificial Sequence
<220> FEATURE:
<223> OTHER INFORMATION: Designed primer based on Clostridium coccoides
      group

<400> SEQUENCE: 1
aaatgacggt acctgactaa                                                   20

<210> SEQ ID NO 2
<211> LENGTH: 22
<212> TYPE: DNA
<213> ORGANISM: Artificial Sequence
<220> FEATURE:
<223> OTHER INFORMATION: Designed primer based on Clostridium coccoides
      group

<400> SEQUENCE: 2
ctttgagttt cattcttgcg aa                                                22

<210> SEQ ID NO 3
<211> LENGTH: 16
<212> TYPE: DNA
<213> ORGANISM: Artificial Sequence
<220> FEATURE:
<223> OTHER INFORMATION: Designed primer based on Clostridium leptum
      subgroup

<400> SEQUENCE: 3
gcacaagcag tggagt                                                       16

<210> SEQ ID NO 4
<211> LENGTH: 18
<212> TYPE: DNA
<213> ORGANISM: Artificial Sequence
<220> FEATURE:
<223> OTHER INFORMATION: Designed primer based on Clostridium leptum
      subgroup

<400> SEQUENCE: 4
cttcctccgt tttgtcaa                                                     18

<210> SEQ ID NO 5
<211> LENGTH: 21
<212> TYPE: DNA
<213> ORGANISM: Artificial Sequence
<220> FEATURE:
<223> OTHER INFORMATION: Designed primer based on Bacteroides fragilis
      group

<400> SEQUENCE: 5
ayagcctttc gaaagraaga t                                                 21

<210> SEQ ID NO 6
<211> LENGTH: 21
<212> TYPE: DNA
<213> ORGANISM: Artificial Sequence
<220> FEATURE:
<223> OTHER INFORMATION: Designed primer based on Bacteroides fragilis
      group

<400> SEQUENCE: 6
ccagtatcaa ctgcaatttt a                                                 21

<210> SEQ ID NO 7
<211> LENGTH: 17
<212> TYPE: DNA
<213> ORGANISM: Artificial Sequence
```

```
<220> FEATURE:
<223> OTHER INFORMATION: Designed primer based on Genus Bifidobacterium

<400> SEQUENCE: 7
ctcctggaaa cgggtgg                                                    17

<210> SEQ ID NO 8
<211> LENGTH: 22
<212> TYPE: DNA
<213> ORGANISM: Artificial Sequence
<220> FEATURE:
<223> OTHER INFORMATION: Designed primer based on Genus Bifidobacterium

<400> SEQUENCE: 8
ggtgttcttc ccgatatcta ca                                              22

<210> SEQ ID NO 9
<211> LENGTH: 17
<212> TYPE: DNA
<213> ORGANISM: Artificial Sequence
<220> FEATURE:
<223> OTHER INFORMATION: Designed primer based on Atopobium cluster

<400> SEQUENCE: 9
gggttgagag accgacc                                                    17

<210> SEQ ID NO 10
<211> LENGTH: 18
<212> TYPE: DNA
<213> ORGANISM: Artificial Sequence
<220> FEATURE:
<223> OTHER INFORMATION: Designed primer based on Atopobium cluster

<400> SEQUENCE: 10
cggrgcttct tctgcagg                                                   18

<210> SEQ ID NO 11
<211> LENGTH: 20
<212> TYPE: DNA
<213> ORGANISM: Artificial Sequence
<220> FEATURE:
<223> OTHER INFORMATION: Designed primer based on Genus Prevotella

<400> SEQUENCE: 11
cacrgtaaac gatggatgcc                                                 20

<210> SEQ ID NO 12
<211> LENGTH: 16
<212> TYPE: DNA
<213> ORGANISM: Artificial Sequence
<220> FEATURE:
<223> OTHER INFORMATION: Designed primer based on Genus Prevotella

<400> SEQUENCE: 12
ggtcgggttg cagacc                                                     16

<210> SEQ ID NO 13
<211> LENGTH: 18
<212> TYPE: DNA
<213> ORGANISM: Artificial Sequence
<220> FEATURE:
<223> OTHER INFORMATION: Designed primer based on Clostridium
        perfringens

<400> SEQUENCE: 13
gggggtttca acacctcc                                                   18
```

<210> SEQ ID NO 14
<211> LENGTH: 18
<212> TYPE: DNA
<213> ORGANISM: Artificial Sequence
<220> FEATURE:
<223> OTHER INFORMATION: Designed primer based on Clostridium
      perfringens

<400> SEQUENCE: 14
gcaagggatg tcaagtgt                                              18

<210> SEQ ID NO 15
<211> LENGTH: 23
<212> TYPE: DNA
<213> ORGANISM: Artificial Sequence
<220> FEATURE:
<223> OTHER INFORMATION: Designed primer based on Family
      Enterobacteriaceae

<400> SEQUENCE: 15
tgccgtaact tcgggagaag gca                                        23

<210> SEQ ID NO 16
<211> LENGTH: 22
<212> TYPE: DNA
<213> ORGANISM: Artificial Sequence
<220> FEATURE:
<223> OTHER INFORMATION: Designed primer based on Family
      Enterobacteriaceae

<400> SEQUENCE: 16
tcaaggacca gtgttcagtg tc                                         22

<210> SEQ ID NO 17
<211> LENGTH: 17
<212> TYPE: DNA
<213> ORGANISM: Artificial Sequence
<220> FEATURE:
<223> OTHER INFORMATION: Designed primer based on Lactobacillus casei
      subgroup

<400> SEQUENCE: 17
accgcatggt tcttggc                                               17

<210> SEQ ID NO 18
<211> LENGTH: 20
<212> TYPE: DNA
<213> ORGANISM: Artificial Sequence
<220> FEATURE:
<223> OTHER INFORMATION: Designed primer based on Lactobacillus casei
      subgroup

<400> SEQUENCE: 18
ccgacaacag ttactctgcc                                            20

<210> SEQ ID NO 19
<211> LENGTH: 27
<212> TYPE: DNA
<213> ORGANISM: Artificial Sequence
<220> FEATURE:
<223> OTHER INFORMATION: Designed primer based on Lactobacillus gasseri
      subgroup

<400> SEQUENCE: 19
gatgcatagc cgagttgaga gactgat                                    27

<210> SEQ ID NO 20
<211> LENGTH: 25
<212> TYPE: DNA
<213> ORGANISM: Artificial Sequence
<220> FEATURE:
<223> OTHER INFORMATION: Designed primer based on Lactobacillus gasseri
      subgroup

<400> SEQUENCE: 20
taaaggccag ttactacctc tatcc                                              25

<210> SEQ ID NO 21
<211> LENGTH: 25
<212> TYPE: DNA
<213> ORGANISM: Artificial Sequence
<220> FEATURE:
<223> OTHER INFORMATION: Designed primer based on Lactobacillus
      plantarum subgroup

<400> SEQUENCE: 21
ctctggtatt gattggtgct tgcat                                              25

<210> SEQ ID NO 22
<211> LENGTH: 24
<212> TYPE: DNA
<213> ORGANISM: Artificial Sequence
<220> FEATURE:
<223> OTHER INFORMATION: Designed primer based on Lactobacillus
      plantarum subgroup

<400> SEQUENCE: 22
gttcgccact cactcaaatg taaa                                               24

<210> SEQ ID NO 23
<211> LENGTH: 16
<212> TYPE: DNA
<213> ORGANISM: Artificial Sequence
<220> FEATURE:
<223> OTHER INFORMATION: Designed primer based on Lactobacillus reuteri
      subgroup

<400> SEQUENCE: 23
gaacgcaytg gcccaa                                                        16

<210> SEQ ID NO 24
<211> LENGTH: 19
<212> TYPE: DNA
<213> ORGANISM: Artificial Sequence
<220> FEATURE:
<223> OTHER INFORMATION: Designed primer based on Lactobacillus reuteri
      subgroup

<400> SEQUENCE: 24
tccattgtgg ccgatcagt                                                     19

<210> SEQ ID NO 25
<211> LENGTH: 21
<212> TYPE: DNA
<213> ORGANISM: Artificial Sequence
<220> FEATURE:
<223> OTHER INFORMATION: Designed primer based on Lactobacillus ruminis
      subgroup

<400> SEQUENCE: 25
caccgaatgc ttgcaytcac c                                                  21

-continued

```
<210> SEQ ID NO 26
<211> LENGTH: 19
<212> TYPE: DNA
<213> ORGANISM: Artificial Sequence
<220> FEATURE:
<223> OTHER INFORMATION: Designed primer based on Lactobacillus ruminis
      subgroup

<400> SEQUENCE: 26
gccgcgggtc catccaaaa                                                 19

<210> SEQ ID NO 27
<211> LENGTH: 22
<212> TYPE: DNA
<213> ORGANISM: Artificial Sequence
<220> FEATURE:
<223> OTHER INFORMATION: Designed primer based on Lactobacillus sakei
      subgroup

<400> SEQUENCE: 27
cataaaacct amcaccgcat gg                                             22

<210> SEQ ID NO 28
<211> LENGTH: 27
<212> TYPE: DNA
<213> ORGANISM: Artificial Sequence
<220> FEATURE:
<223> OTHER INFORMATION: Designed primer based on Lactobacillus sakei
      subgroup

<400> SEQUENCE: 28
tcagttacta tcagatacrt tcttctc                                        27

<210> SEQ ID NO 29
<211> LENGTH: 24
<212> TYPE: DNA
<213> ORGANISM: Artificial Sequence
<220> FEATURE:
<223> OTHER INFORMATION: Designed primer based on Lactobacillus brevis

<400> SEQUENCE: 29
attttgtttg aaaggtggct tcgg                                           24

<210> SEQ ID NO 30
<211> LENGTH: 25
<212> TYPE: DNA
<213> ORGANISM: Artificial Sequence
<220> FEATURE:
<223> OTHER INFORMATION: Designed primer based on Lactobacillus brevis

<400> SEQUENCE: 30
acccttgaac agttactctc aaagg                                          25

<210> SEQ ID NO 31
<211> LENGTH: 23
<212> TYPE: DNA
<213> ORGANISM: Artificial Sequence
<220> FEATURE:
<223> OTHER INFORMATION: Designed primer based on Lactobacillus
      fermentum

<400> SEQUENCE: 31
cctgattgat tttggtcgcc aac                                            23

<210> SEQ ID NO 32
<211> LENGTH: 26
<212> TYPE: DNA
```

```
<213> ORGANISM: Artificial Sequence
<220> FEATURE:
<223> OTHER INFORMATION: Designed primer based on Lactobacillus
      fermentum

<400> SEQUENCE: 32
acgtatgaac agttactctc atacgt                                           26

<210> SEQ ID NO 33
<211> LENGTH: 20
<212> TYPE: DNA
<213> ORGANISM: Artificial Sequence
<220> FEATURE:
<223> OTHER INFORMATION: Designed primer based on Genus Enterococcus

<400> SEQUENCE: 33
atcagagggg gataacactt                                                  20

<210> SEQ ID NO 34
<211> LENGTH: 21
<212> TYPE: DNA
<213> ORGANISM: Artificial Sequence
<220> FEATURE:
<223> OTHER INFORMATION: Designed primer based on Genus Enterococcus

<400> SEQUENCE: 34
actctcatcc ttgttcttct c                                                21

<210> SEQ ID NO 35
<211> LENGTH: 30
<212> TYPE: DNA
<213> ORGANISM: Artificial Sequence
<220> FEATURE:
<223> OTHER INFORMATION: Designed primer based on Genus Staphylococcus

<400> SEQUENCE: 35
tttgggctac acacgtgcta caatggacaa                                       30

<210> SEQ ID NO 36
<211> LENGTH: 24
<212> TYPE: DNA
<213> ORGANISM: Artificial Sequence
<220> FEATURE:
<223> OTHER INFORMATION: Designed primer based on Genus Staphylococcus

<400> SEQUENCE: 36
aacaacttta tgggatttgc wtga                                             24

<210> SEQ ID NO 37
<211> LENGTH: 23
<212> TYPE: DNA
<213> ORGANISM: Artificial Sequence
<220> FEATURE:
<223> OTHER INFORMATION: Designed primer based on Genus Pseudomonas

<400> SEQUENCE: 37
caaaactact gagctagagt acg                                              23
```

```
<210> SEQ ID NO 38
<211> LENGTH: 25
<212> TYPE: DNA
<213> ORGANISM: Artificial Sequence
<220> FEATURE:
<223> OTHER INFORMATION: Designed primer based on Genus Pseudomonas

<400> SEQUENCE: 38
taagatctca aggatcccaa cggct                                   25
```

MARKER AND METHOD FOR DETERMINATION OF PARKINSON'S DISEASE

TECHNICAL FIELD

The present invention relates to a marker and a method for determining Parkinson's disease.

BACKGROUND ART

Parkinson's disease (PD) is known as a neurodegenerative disease which increases with aging, and the number of patients worldwide is estimated to reach 10 million by 2030. Study on healthy subjects also found α-synuclein-positive Lewy bodies in the gastrointestinal tract, olfactory tissue, and heart, although no PD symptoms were present, and suggests that these histological lesions occur before the onset, and the PD pathological condition gradually progresses to the central nervous system too.

Similarly, it was revealed that α-synuclein appears in the intestines of PD patients 20 years before the onset (Non-Patent Literature 1). In addition to these findings, olfactometry (Non-Patent Literature 2) and MIBG myocardial scintigraphy (Non-Patent Literature 3) are regarded as useful for discrimination of early PD, and presence of lesions in peripheral organs is suggested. Constipation is a symptom observed before the onset of PD, and the cohort study in Honolulu revealed that constipation occurs 10 years or more before the onset of PD on average (Non-Patent Literature 4).

CITATION LIST

Non-Patent Literature

Non-Patent Literature 1: Hawkes C H, et al., Parkinsonism Relat. Disord., 2010, 16(2): 79-84
Non-Patent Literature 2: Katzenschlager R, et al., Curr. Opin. Neurol., 2004, 17(4): 417-423
Non-Patent Literature 3: Hirayama M, et al., J. Auton. Nerv. Syst., 1995, 53(2-3): 230-234
Non-Patent Literature 4: Abbott R D, et al., Neurology, 2001, 57(3): 456-462

SUMMARY OF INVENTION

Technical Problem

There is no knowledge about the change with time in microbiota in the intestine of a single PD patient. There is a need for a method for simply determining the progress of the pathological condition of PD.

Solution to Problem

In view of the above-mentioned problems, the present inventors have studied whether a change with time in the microbiota in a single patient is involved in a change in the disease condition or not in order to clarify a relationship between the change in the PD pathological condition and intestinal bacteria, and conducted measurement of intestinal microbiota and blood components and a 2-year perspective study for PD patients and housemates thereof. As a result, they found that the degree of deterioration of the PD condition can be determined by measuring an in vivo increase or decrease of intestinal bacteria of the PD patient and that intestinal bacteria can be a marker for detection of PD, and the present invention was accomplished. In addition, they found that deterioration of the PD condition can be determined by using the blood lipopolysaccharide (LPS) level or the blood lipopolysaccharide-binding protein (LBP) level as an indicator.

That is, the present invention relates to the following aspects [1] to [14]:

[1] A marker for determination of Parkinson's disease, the marker being the number of one or more intestinal bacteria selected from the group consisting of *Bifidobacterium*, *Bacteroides fragilis* group, *Lactobacillus brevis*, and *Lactobacillus plantarum* subgroup and/or the total number of intestinal bacteria.

[2] The marker according to [1], wherein the determination of Parkinson's disease is determination of a risk of deterioration of Parkinson's disease.

[3] The marker according to [2], wherein the deterioration of Parkinson's disease is deterioration of a constipation symptom or a psychiatric symptom.

[4] The marker according to [3], wherein the psychiatric symptom is one or more selected from the group consisting of hallucination, cognition, and motivation.

[5] A method for determining deterioration of a disease condition of a Parkinson's disease patient, comprising measuring the numbers of one or more intestinal bacteria selected from the group consisting of *Bifidobacterium*, *Bacteroides fragilis* group, *Lactobacillus brevis*, and *Lactobacillus plantarum* subgroup and/or the total numbers of intestinal bacteria in the patient at two or more different time points and comparing the numbers.

[6] The method according to [5], wherein the deterioration of a disease condition of a Parkinson's disease patient is deterioration of a constipation symptom or a psychiatric symptom.

[7] The method according to [6], wherein the psychiatric symptom is one or more selected from the group consisting of hallucination, cognition, and motivation.

[8] A marker for determination of Parkinson's disease, the marker being a blood LPS level and/or a blood LBP level.

[9] The marker according to [8], wherein the determination of Parkinson's disease is determination of a risk of deterioration of Parkinson's disease.

[10] The marker according to [9], wherein the deterioration of Parkinson's disease is deterioration of a constipation symptom or a psychiatric symptom.

[11] The marker according to [10], wherein the psychiatric symptom is one or more selected from the group consisting of hallucination, cognition, and motivation.

[12] A method for determining deterioration of a disease condition of a Parkinson's disease patient, comprising measuring blood LPS levels and/or blood LBP levels of the patient at two or more different time points and comparing the levels.

[13] The method according to [12], wherein the deterioration of a disease condition of a Parkinson's disease patient is deterioration of a constipation symptom or a psychiatric symptom.

[14] The method according to [13], wherein the psychiatric symptom is one or more selected from the group consisting of hallucination, cognition, and motivation.

[15] A kit for conducting the method according to any one of [5] to [7], the kit comprising a protocol for measuring intestinal bacteria according to any one of [1] to [4].

Advantageous Effects of Invention

According to the present invention, a risk of deterioration of PD can be determined by measuring the number of specific intestinal bacteria or by measuring the numbers of specific intestinal bacteria at two or more different time points and comparing the numbers. In addition, deterioration of PD can be determined by comparing the blood LPS levels or blood LBP levels.

DESCRIPTION OF EMBODIMENTS

Figure 1:
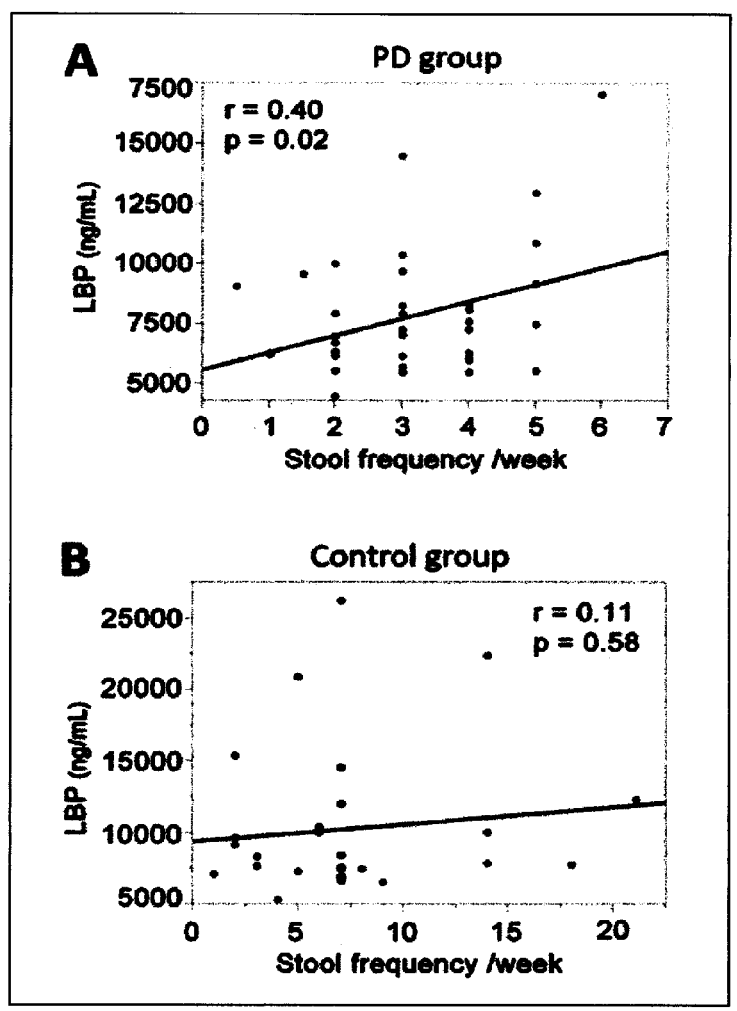
FIG. 1 shows a correlation between the serum LBP level and the frequency of excretion (A: PD group, B: Control group).

The marker for determination of PD of the present invention is the number of one or more intestinal bacteria selected from the group consisting of *Bifidobacterium, Bacteroides fragilis* group, *Lactobacillus brevis*, and *Lactobacillus plantarum* subgroup and/or the total number of intestinal bacteria. Although it is known that these intestinal bacteria are present in the human intestine, it has not been reported about the relationship between these intestinal bacteria and the progress of PD condition. Here, the total number of intestinal bacteria is, for example, the total bacterial number measured by a DAPI counting method but is not limited thereto. The total bacterial number may be the sum of the bacterial numbers of a plurality of dominant bacterial species in the intestine, which corresponds to about 70% or more of the total bacterial number measured by the DAPI counting method. Examples of the total bacterial number include the sum of the bacterial numbers of 19 bacterial species shown in Example (Table 1) below.

As described in Example below, there was a significant correlation between the number of the intestinal bacteria in feces of a PD patient and deterioration of the condition of PD. Specifically, a decrease in the number of at least one, preferably two or more, intestinal bacteria selected from the group consisting of *Bifidobacterium, Bacteroides fragilis* group, *Lactobacillus brevis*, and *Lactobacillus plantarum* subgroup and/or in the total number of intestinal bacteria indicates an increase in the risk of deterioration of PD.

Here, deterioration of PD or deterioration of the condition of a PD patient means that the disease condition actually progresses and becomes severe. A risk of deterioration of PD or a risk of deterioration of the condition of a PD patient refers to a possibility that the condition of PD will further deteriorate in the future compared to the actual current disease condition.

The risk of deterioration of PD may be determined by measuring the number of the intestinal bacteria in a sample and applying the number to an approximate line equation (for example, approximate line equations shown in Example (e.g., FIGS. 2, 3, 5, and 6) below) created in advance for a correlation between the number of the intestinal bacteria and the deterioration of disease condition. Examples of the sample include subject-derived biological samples, for example, digestive tract contents such as intestinal fluid and feces. Because of its non-invasiveness, feces is preferred as a sample.

In addition, a significant correlation was also observed between the blood LBP level and constipation, which is a typical symptom of PD. That is, it is inferred that the LBP level decreases in a group where the stool frequency is low (being constipation symptom) and the PD condition is probably getting worse and that the LBP level increases in a group where the stool frequency is high (not being constipation symptom) and the PD condition is probably mild. In PD patients, since the LBP level and the LPS level inversely correlate with each other, it is inferred that the LPS level increases in the group where the PD condition is getting worse and that the LPS level decreases in the group where the PD condition is mild. Accordingly, the deterioration of PD can be determined by examining the change in the blood LPS level and/or the blood LBP level.

Specifically, in order to determine deterioration of the disease condition of a PD patient, it is possible to perform the determination by measuring the numbers of one or more intestinal bacteria selected from the group consisting of *Bifidobacterium, Bacteroides fragilis* group, *Lactobacillus brevis*, and *Lactobacillus plantarum* subgroup and/or the total numbers of intestinal bacteria in the patient at two or more different time points and comparing the measured bacterial numbers.

Measurement at two or more time points refers to that measurement of the intestinal bacteria is performed at a time point and is then performed at one or more time points after a certain interval. The interval varies depending on, for example, the condition and the pathological condition of the patient and is not particularly limited. For example, an arbitrary period of 1 week to 5 years, such as 1 week, 2 weeks, 3 weeks, 4 weeks, 1 month, 2 months, 3 months, 6 months, 9 months, 1 year, 2 years, 3 years, 4 years, or 5 years is suitably selected.

In determination of deterioration of the disease condition of a PD patient, when the numbers of the intestinal bacteria in a single PD patient are measured at two or more different time points, if the number of the intestinal bacteria results in a decreased tendency, it can be determined that the PD is getting severe. In contrast, if the number of the intestinal bacteria results in an increased tendency, it can be determined that the PD is getting mild. Specifically, if the number of one or more bacteria selected from the group consisting of *Bifidobacterium*, *Bacteroides fragilis* group, *Lactobacillus brevis*, and *Lactobacillus plantarum* subgroup and/or the total number of intestinal bacteria is decreased, it can be determined that the PD condition is getting severe, and in contrast, when the number is increased, it can be determined that the condition is getting mild.

In determination of PD (determination of a risk of deterioration of PD or determination of deterioration of the PD symptom), it is possible to perform the determination by measuring the number of the intestinal bacteria in a sample and comparing whether the number is larger or smaller than a reference which is the value (P) of the vertical axis at the time point of 0 in the horizontal axis in an approximate line equation created in advance for a correlation between the number of the intestinal bacteria (vertical axis) and the deterioration of disease condition (horizontal axis). In addition, it is also possible to perform the determination by comparing whether an amount of change in the number of the intestinal bacteria is larger or smaller than a reference which is the value (Q) of the vertical axis at the time point of 0 in the horizontal axis in an approximate line equation created in advance for a correlation between the amount of change in the number of the intestinal bacteria measured at two or more different time points (vertical axis) and the deterioration of disease condition (horizontal axis) of a single PD patient. For example, based on the approximate line equation shown in Example (e.g., FIGS. 2, 3, 5, and 6) below, when one or more of the following references are satisfied, it can be determined that the risk of deterioration of PD is high or the possibility of deterioration of PD symptom is high. These references can also be used in combination.

(1) The number of *Bifidobacterium* per 1 gram of a sample at an arbitrary time point is less than $P_1$ cells ($P_1$: the value of the vertical axis at the time point of 0 in the horizontal axis in FIG. 2B).

(2) The number of *Bacteroides fragilis* group per 1 gram of a sample at an arbitrary time point is less than $P_2$ cells ($P_2$: the value of the vertical axis at the time point of 0 in the horizontal axis in FIG. 2A).

(3) The number of *Lactobacillus brevis* per 1 gram of a sample at an arbitrary time point is less than $P_3$ cells ($P_3$: the value of the vertical axis at the time point of 0 in the horizontal axis in FIG. 3B or 3D).

(4) The number of *Lactobacillus plantarum* subgroup per 1 gram of a sample at an arbitrary time point is less than $P_4$ cells ($P_4$: the value of the vertical axis at the time point of 0 in the horizontal axis in FIG. 3A or 3C).

(5) The amount of change in the total number of intestinal bacteria per 1 gram of a sample at two or more time points is less than $Q_1$ cells ($Q_1$: the value of the vertical axis at the time point of 0 in the horizontal axis in FIG. 5B).

(6) The amount of change in the number of *Bifidobacterium* per 1 gram of a sample at two or more time points is less than $Q_2$ cells ($Q_2$: the value of the vertical axis at the time point of 0 in the horizontal axis in FIG. 5A).

In addition, deterioration of PD of a patient can be determined by measuring the blood LPS levels and/or the blood LBP levels of the PD patient at two or more different time points and comparing the measured levels (between the LPS levels or between the LBP levels). The phrase "two or more time points" has the same meaning as described above. The blood levels of LPS and/or LBP are preferably serum levels.

In the determination of the degree of severity of PD, when the LPS levels and/or the LBP levels of a single PD patient are measured at two or more different time points, if the LPS level results in an increased tendency, it can be determined that the PD is getting severe. In contrast, if the LPS level results in a decreased tendency, it can be determined that the PD is getting mild. If the LBP level results in a decreased tendency, it can be determined that the PD is getting severe, and in contrast, the LBP level results in an increased tendency, it can be determined that the PD is getting mild.

In the present invention, the measurement of intestinal bacteria in a sample include measurement (quantification) of the number of intestinal bacteria. Examples of the method for measuring the number of intestinal bacteria in a sample include a method involving culturing intestinal bacteria in an appropriate medium and counting the number of the bacteria, a method involving culturing intestinal bacteria in a liquid selection medium and measuring the turbidity or absorbance, a FISH method, and a quantitative RT-PCR method (RT-qPCR method). Among these methods, the RT-qPCR method is preferable.

The RT-PCR method will now be described. The analytical method by the RT-PCR method can be performed by, for example, (1) a step of extracting RNA of a bacterium of interest in a sample, (2) a step of synthesizing cDNA by a reverse transcription (RT) reaction using a nucleic acid fragment (primer) that hybridizes to the extracted RNA and subsequently performing PCR using the cDNA as a template, and (3) a step of detecting the DNA fragment amplified in the step (2). A DNA fragment (PCR product) specific to the intestinal bacterium of interest can be obtained by combining the nucleic acid fragment with the template cDNA derived from a sample and performing amplification reaction. The number of the intestinal bacterium of interest in the sample can be determined by observing the PCR product over time and identifying the number of PCR cycles at the time when the amount of DNA reaches a certain level.

The observation of an amplified PCR product over time can be performed by labeling the PCR product with an intercalating fluorescent dye, such as SYBR® Green I, and measuring the fluorescence intensity at each PCR cycle. An intercalating dye has a property of being intercalated in a double-stranded nucleic acid and thereby increasing the fluorescence intensity and therefore it is possible to precisely measure the PCR product generated from cDNA of a target bacterium by PCR reaction. In particular, SYBR® Green I is suitably used.

The intestinal bacterium of interest in a sample can be quantitatively determined by identifying the number of PCR cycles (threshold cycle: $C_T$) when the fluorescence intensity (DNA amount) reaches a certain level that has been arbitrarily set. In addition, for example, a TaqMan probe or molecular beacon labeled with a fluorescent dye can also be used. The TaqMan probe and the molecular beacon are each a probe in which a fluorescent dye and a quencher are bonded to an oligonucleotide having homology with the internal sequence of the region to be amplified by PCR and are used in the PCR reaction by existing together. Since fluorescence is emitted according to the PCR amplification reaction by the interaction between the fluorescent dye and the quencher bounded to the probe, the amplified PCR product can be observed over time by measuring the fluorescence intensity at each PCR cycle.

The intestinal bacterium of interest in a sample can be quantitatively determined by a calibration curve of the logarithmic values of the bacterial numbers measured by, for example, a DAPI counting method or a culture method and the $C_T$ values. That is, a calibration curve is created in advance by plotting the logarithmic values of the bacterial numbers of a target on the horizontal axis and the $C_T$ values on the vertical axis, and the $C_T$ value obtained as a result of PCR reaction is applied to the calibration curve to quantify the intestinal bacterium of interest in the sample.

In order to implement the method for determining PD of the present invention, it is preferable to use a kit including a protocol for measuring the intestinal bacteria in a sample. The kit includes a measuring reagent for the marker of the present invention and a protocol (a protocol describing, for example, a method for measuring intestinal bacteria and a method for determining PD, in particular, a reference for determining the degree of severity, and factors that influence the measurement results and the degree of the influence). The determination can be performed as in the above-described determination method by using the reference. Here, examples of the measuring reagent for the marker include a reagent for measuring the number of the intestinal bacteria described above, a reagent for detecting mRNA, and a reagent for detecting DNA.

The bacterial number in vivo varies depending on, for example, the living environment and eating habits of each patient. The status of the progress of PD can be determined by comparing the bacterial numbers in samples of a single patient measured time-serially.

EXAMPLES

The present invention will now be described in detail by way of examples but is not limited thereto.
Bacterial Strain Used Bacterial strains stored in the Yakult Central Institute, Yakult Honsha Co., Ltd. shown in Table 1 were used. The initial bacterial number of each bacterial strain was adjusted to about $1 \times 10^4$ cells.

The culture conditions of each bacterial strain are shown in Table 1. The details of culture conditions A and B are as follows.

Condition A: static culture was performed in a 1% glucose addition modified GAM broth at 37° C. under an anaerobic condition for 24 to 72 hours.

Condition B: static culture was performed in an MRS broth at 37° C. under an anaerobic condition for 24 to 72 hours.

Condition C: static culture was performed in a BHI broth at 37° C. under an aerobic condition for 18 hours.

These bacterial cells were counted by a DAPI method and were then appropriately diluted to a certain bacterial number to prepare each bacterial liquid.

TABLE 1

| Taxon | Strain | Culture condition |
| --- | --- | --- |
| Clostridium coccoides group | Blautia producta JCM 1471 (ATCC 27340) | Condition A |
| Clostridium leptum subgroup | Faecalibacterium prausnitzii ATCC 27768 | Condition A |
| Bacteroides fragilis group | Bacteroides vulgatus ATCC 8482 | Condition A |
| Bifidobacterium | Bifidobacterium adolescentis ATTC 15703 | Condition A |
| Atopobium cluster | Collinsella aerofaciens DSM 3979 | Condition A |
| Genus Prevotella | Prevotella melaninogenica ATCC 25845 | Condition A |
| Clostridium perfringens | Clostridium perfringens JCM 1290 (ATCC 13124) | Condition A |
| Family Enterobacteriaceae | Escherichia coli JCM 1649 (ATCC 11775) | Condition C |
| Lactobacillus casei subgroup | Lactobacillus casei ATCC 334 | Condition B |
| Lactobacillus gasseri subgroup | Lactobacillus acidophilus ATCC 4356 | Condition B |
| Lactobacillus plantarum subgroup | Lactobacillus plantarum ATCC 14917 | Condition B |
| Lactobacillus reuteri subgroup | Lactobacillus reuteri JCM 1112 (ATCC 23272) | Condition B |
| Lactobacillus ruminis subgroup | Lactobacillus ruminis JCM 1152 (ATCC 27780) | Condition B |
| Lactobacillus sakei subgroup | Lactobacillus sakei JCM 1157 (ATCC 15521) | Condition B |
| Lactobacillus brevis | Lactobacillus brevis ATCC 14869 | Condition B |
| Lactobacillus fermentum | Lactobacillus fermentum ATCC 14931 | Condition B |
| Genus Enterococcus | Enterococcus faecalis ATCC 19433 | Condition B |
| Genus Staphylococcus | Staphylococcus aureus GIFU 9120 (ATCC 12600) | Condition C |
| Genus Pseudomonas | Pseudomonas aeruginosa IFO 12689 | Condition C |

Reference Example 1

Preparation of Specific Primer

Table 2 shows each primer used in measurement of the number of the intestinal bacteria. Table 2 also shows literatures describing each primer.

TABLE 2

| Target gene | Primer name | Sequence (5'-3') | SEQ ID NO: | Literature |
| --- | --- | --- | --- | --- |
| Clostridium coccoides group | g-Ccoc-F | AAATGACGGTACCTGACTAA | 1 | 1 |
|  | g-Ccoc-R | CTTTGAGTTTCATTCTTGCGAA | 2 | 1 |
| Clostridium leptum subgroup | sg-Clept-F | GCACAAGCAGTGGAGT | 3 | 2 |
|  | sg-Clept-R | CTTCCTCCGTTTTGTCAA | 4 | 2 |
| Bacteroides fragilis group | g-Bfra-F2 | AYAGCCTTTCGAAAGRAAGAT | 5 | 3 |
|  | g-Bfra-R | CCAGTATCAACTGCAATTTTA | 6 | 1 |
| Genus Bifidobacterium | g-Bifid-F | CTCCTGGAAACGGGTGG | 7 | 1 |
|  | g-Bifid-R | GGTGTTCTTCCCGATATCTACA | 8 | 1 |

TABLE 2-continued

| Target gene | Primer name | Sequence (5'-3') | SEQ ID NO: | Literature |
|---|---|---|---|---|
| Atopobium cluster | c-Atopo-F | GGGTTGAGAGACCGACC | 9 | 2 |
| | c-Atopo-R | CGGRGCTTCTTCTGCAGG | 10 | 2 |
| Genus Prevotella | g-Prevo-F | CACRGTAAACGATGGATGCC | 11 | 1 |
| | g-Prevo-R | GGTCGGGTTGCAGACC | 12 | 1 |
| Clostridium perfringens | s-Clper-F | GGGGGTTTCAACACCTCC | 13 | 4 |
| | ClPER-R | GCAAGGGATGTCAAGTGT | 14 | 5 |
| Family Enterobacteriaceae | f-Enbac-F | TGCCGTAACTTCGGGAGAAGGCA | 15 | 6 |
| | f-Enbac-R | TCAAGGACCAGTGTTCAGTGTC | 16 | 6 |
| Lactobacillus casei subgroup | sg-Lcas-F | ACCGCATGGTTCTTGGC | 17 | 4 |
| | sg-Lcas-R | CCGACAACAGTTACTCTGCC | 18 | 4 |
| Lactobacillus gasseri subgroup | sg-Lgas-F | GATGCATAGCCGAGTTGAGAGACAGAT | 19 | 4 |
| | sg-Lgas-R | TAAAGGCCAGTTACTACCTCTATCC | 20 | 4 |
| Lactobacillus plantarum subgroup | sg-Lpla-F | CTCTGGTATTGATTGGTGCTTGCAT | 21 | 4 |
| | sg-Lpla-R | GTTCGCCACTCACTCAAATGTAAA | 22 | 4 |
| Lactobacillus reuteri subgroup | sg-Lrcu-F | GAACGCAYTGGCCCAA | 23 | 4 |
| | sg-Lrcu-R | TCCATTGTGGCCGATCAGT | 24 | 4 |
| Lactobacillus ruminis subgroup | sg-Lrum-F | CACCGAATGCTTGCAYTCACC | 25 | 4 |
| | sg-Lrum-R | GCCGCGGGTCCATCCAAAA | 26 | 4 |
| Lactobacillus sakei subgroup | sg-Lsak-F | CATAAAACCTAMCACCGCATGG | 27 | 4 |
| | sg-Lsak-R | TCAGTTACTATCAGATACRTTCTTCTC | 28 | 4 |
| Lactobacillus brevis | s-Lbrc-F | ATTTTGTTTGAAAGGTGGCTTCGG | 29 | 4 |
| | s-Lbrc-R | ACCCTTGAACAGTTACTCTCAAAGG | 30 | 4 |
| Lactobacillus fermentum | LFer-1 | CCTGATTGATTTTGGTCGCCAAC | 31 | 4 |
| | LFer-2 | ACGTATGAACAGTTACTCTCATACGT | 32 | 4 |
| Genus Enterococcus | g-Encoc-F | ATCAGAGGGGGATAACACTT | 33 | 4 |
| | g-Encoc-R | ACTCTCATCCTTGTTCTTCTC | 34 | 4 |
| Genus Staphylococcus | g-Staph-F | TTTGGGCTACACACGTGCTACAATGGACAA | 35 | 4 |
| | g-Staph-R | AACAACTTTATGGGATTTGCWTGA | 36 | 4 |
| Genus Pseudomonas | PSD7F | CAAAACTACTGAGCTAGAGTACG | 37 | 6 |
| | PSD7R | TAAGATCTCAAGGATCCCAACGGCT | 38 | 6 |

1. Matsuki T, Watanabe K, Fujimoto J, Miyamoto Y, Takada T, Matsumoto K, et al. Development of 16S rRNA-gene-targeted group-specific primers for the detection and identification of predominant bacteria in human feces. Appl Environ Microbiol 2002; 68: 5445-5451.
2. Matsuki T, Watanabe K, Fujimoto J, Takeda T, Tanaka R. Use of 16S rRNA gene-targeted group-specific primers for real-time PCR analysis of predominant bacteria in human feces. Appl Environ Microbiol 2004; 70: 7220-7228.
3. Matsuki T. Development of quantitative PCR detection method with 16S rRNA gene-targeted genus- and species-specific primers for the analysis of human intestinal microflora and its application. Nihon Saikingaku Zasshi 2007; 62: 255-261.
4. Matsuda K, Tsuji H, Asahara T, Matsumoto K, Takada T, Nomoto K. Establishment of an analytical system for the human fecal microbiota, based on reverse transcription-quantitative PCR targeting of multicopy rRNA molecules. Appl Environ Microbiol 2009; 75: 1961-1969.
5. Kikuchi E, Miyamoto Y, Narushima S, Itoh K. Design of species specific primers to identify 13 species of Clostridium harbored in human intestinal tracts. Microbiol Immunol 2002; 46: 353-358.
6. Matsuda K, Tsuji H, Asahara T, Kado Y, Nomoto K. Sensitive quantitative detection of commensal bacteria by rRNA-targeted reverse transcription-PCR. Appl Environ Microbiol 2007; 73: 32-39.

Reference Example 2

Preparation of Calibration Curve to be Used in RT-PCR

A calibration curve to be used in quantification of intestinal bacteria of interest in samples was created. Specifically, according to the procedure shown below, a calibration curve was created by plotting the numbers of intestinal bacteria measured by a DAPI counting method on the horizontal axis and the $C_T$ values on the vertical axis.

1) RNAlater (Arabian, Inc., 400 µL) was added to a bacterial liquid (200 µL) of each bacterial strain prepared in the above paragraph "Bacterial strain used", followed by leaving to stand at room temperature for 5 minutes. Subsequently, centrifugation was performed at 13,000 g for 5 minutes, and the supernatant was removed by decantation. A lysis buffer (450 µL, prepared by mixing 346.5 µL of RLT buffer, 100 µL of TE, and 3.5 µL of β-mercaptomethanol per one sample) and glass beads having a diameter of 0.1 mm (TOMY Seiko Co., Ltd., 300 mg) were added to the residue after the removal of the supernatant.
2) The sample tube was set on a shaker (ShakeMaster) and was then shaken for 5 minutes to disrupt the bacterial cells.
3) Water saturated phenol (500 µL) was added to the sample tube, followed by stirring with a vortex for 5 to 10 seconds.
4) The sample tube was set on a heat block of 60° C., followed by a reaction for 10 minutes (hot phenol method).
5) Chloroform/isoamyl alcohol (24:1, 100 µL) were added to the sample tube, followed by stirring with a vortex for 5 to 10 seconds.
6) After centrifugation (13,000 g, for 5 minutes), 470 µL of the supernatant was transferred to another 1.5-mL microtube with lid.
7) Chloroform/isoamyl alcohol (24:1, 470 µL) were added to the microtube, followed by stirring with a vortex for 5 to 10 seconds.
8) After centrifugation (13,000 g, for 5 minutes), 400 µL of the supernatant was transferred to another 1.5-mL microtube with lid.
9) 3 M Na acetate (pH 5.4, 40 µL) and isopropanol (400 µL) were added to the microtube, followed by inversion mixing.
10) Centrifugation (20,000 g, for 10 minutes) was performed.
11) After removing the supernatant by decantation, 80% ethanol (500 µL) was added to the residue.
12) After centrifugation (20,000 g, for 2 minutes), the supernatant was removed by decantation.
13) After air drying (for about 20 minutes with the opening up), Nuclease-free water (Ambion, Inc.) was added thereto so as to give a concentration of $2\times10^8$ cells/mL based on the number of bacteria measured by a DAPI method, and the mixture was stirred for homogenous dissolution. Furthermore, 10-fold serial dilution with Nuclease-free water was performed. The samples diluted within a range of $2\times10^{-3}$ to $2\times10$ cells/mL were used as RNA samples described in the following 14) and were subjected to RT-qPCR reaction.
14) RT-qPCR was performed using a QIAGEN OneStep RT-PCR Kit (QIAGEN). The composition of reaction solution (the total volume: 10 µL) was composed of 1×QIAGEN OneStep RT-PCR Buffer, 0.5×Q-Solution, 0.4 mM dNTP Mix, 1/25 quantity of QIAGEN OneStep RT-PCR Enzyme Mix, 1/100,000 quantity of SYBR® Green I (Molecular Probes, Inc.), 1×ROX Reference Dye (Invitrogen), 0.60 µM of each primer shown in Table 2, and 5 µL of the RNA sample prepared in the above 13).
15) The reaction solution was subjected to reverse transcription at 50° C. for 30 minutes, and the reverse transcriptase was then inactivated by heating at 95° C. for 15 minutes. Subsequently, a cycle consisting of 94° C. for 20 seconds, 55° C. or 60° C. (55° C. for SEQ ID NOs: 1, 2, and 15 to 28 of Table 2, 60° C. for SEQ ID NOs: 3 to 14, 29, and 30, 55° C. for SEQ ID NOs: 31 to 34, and 60° C. for SEQ ID NOs: 35 to 38) for 20 seconds, and 72° C. for 50 seconds was repeated 45 cycles to obtain an amplification product. The amount of the amplification product was measured at each cycle as the fluorescence intensity of SYBR® Green I to create a PCR curve. The base line and threshold of fluorescence intensity were set, and the number of cycles ($C_T$ value) at which the PCR curve and the threshold intersects each other was determined. The resulting $C_T$ value was plotted on the vertical axis, and the bacterial number of the sample applied to the PCR reaction was plotted on the horizontal axis. In these analyses, Sequence Detection System (SDS) software (Applied Biosystems) was used. In addition, in order to verify whether the amplification by PCR was specifically performed or not, the denaturation temperature was separately measured. The denaturation temperature was measured by producing the amplification product, then performing a reaction at 94° C. for 15 seconds, subsequently raising the temperature slowly from 55° C. or 60° C. to 99° C. at a rate of 0.2° C./sec, plotting the temperature on the horizontal axis and the fluorescence intensity of SYBR® Green I on the vertical axis to create a denaturation curve of the amplification product, and measuring the temperature at which the fluorescence intensity sharply decreases. This series of reactions was performed by an ABI PRISM® 7900HT system (Applied Biosystems).
16) A calibration curve was created by plotting each of the bacterial numbers of intestinal bacteria measured by the DAPI method on the horizontal axis and the $C_T$ values corresponding thereto obtained by RT-qPCR on the vertical axis.

Example 1

(1) Relationship Between PD and Intestinal Microbiota

The intestinal microbiota of PD patients was examined carefully to evaluate the relationship between PD and intestinal microbiota.

Recruited were 52 PD patients (male: 21, female: 31, age: 68.9±6.8) and 36 partners of the patients (male: 21, female: 15, age: 68.4±9.7) as controls. The clinical symptoms of PD were evaluated using Hoehn-Yater (HY) severity classification and unified Parkinson's disease rating scale (UPDRS) Parts 1 to 4.

Among the recruited PD patients, 42 patients could be followed-up for 2 years. Furthermore, 6 patients who were found to have another disease during follow-up were excluded. Consequently, 36 patients in total were studied as subjects.

(2) Biochemical Test

The serum lipopolysaccharide (LPS)-binding protein (LBP) level was measured with an ELISA kit (HK315-01, Hycult Biotech). The diamine oxidase (DAO) level was measured with an ELISA kit (K8500, Immundiagnostik AG).

(3) Measurement of Bacterial Number in Feces by RT-qPCR Targeting rRNA (a) Preparation of Sample for RNA Extraction RNAlater (Arabian, Inc., 0.2 mL) was added to feces (4 mg) collected from a patient or a control, followed by leaving to stand at room temperature for 5 minutes. Subsequently, centrifugation was performed at 14,000 g for 10 minutes, the supernatant was removed by decantation, and the residue was then used as a sample for RNA extraction.

(b) Nucleic Acid Extraction

RNA was extracted according to the following procedure.
1) A lysis buffer (450 µL, prepared by mixing 346.5 µL of RLT buffer, 100 µL of TE, and 3.5 µL of β-mercaptoethanol per one sample) and glass beads having a diameter of 0.1 mm (300 mg) were added to the sample for RNA extraction prepared in the above (a).

2) Nucleic acid was extracted as in the method described in 2) to 12) of Reference Example 2.

3) After air drying (for about 20 minutes with the opening up), Nuclease-free water (200 μL) was added thereto, and the mixture was stirred for homogenous dissolution to prepare an RNA sample.

(c) Measurement of Bacterial Number

The RNA sample prepared in (b) was subjected to measurement of bacterial number using an RT-qPCR method. The RT-qPCR was performed as in the method described in 14) and 15) of Reference Example 2.

(4) Statistical Analysis

Statistical analysis was performed by JMP Pro statistical software package version 11.0.0 (SAS Institute, Cary, NC). The analytical results are shown as mean±standard deviation. Mann-Whitney's U-test and Student's t-test were used for comparison between groups, and Spearman's correlation analysis was used for correlation analysis. A p value of 0.05 or less or a correlation coefficient of 0.3 or more was regarded as statistically significant. Outliers that were apparent in Smirnov's rejection test were rejected.

Results (1) Patient Information

Table 3 shows score information on each parameter when the subjects were divided into healthy subjects and PD patients.

TABLE 3

| Patient information | | |
|---|---|---|
| | Healthy subject (control)[a] | PD[a] |
| Sex (actual number) | | |
| Male | 21 | 21 |
| Female | 15 | 31 |
| Total | 36 | 52 |
| Age (year) | 68.4 ± 9.7 | 68.9 ± 6.8 |
| LBP level | 10140 ± 5061 | 7785 ± 2406 |
| Stool frequency (/week) | 7.6 ± 4.6 | 3.1 ± 1.2 |
| Disease duration (year) | — | 9.5 ± 5.4 |
| UPDRS Part 1 (Mentation, behavior, and mood) score | — | 2.9 ± 2.3 |
| UPDRTS Part 2 (Activities of daily living) | — | 11.7 ± 6.8 |
| UPDRS Part 3 (Motor examination) score | — | 25.6 ± 11.8 |
| UPDRS Part 4 (Complicartion of therapy) score | — | 3.4 ± 2.4 | a: Showing Mean and Standard Deviation.

Table 3 demonstrates that the stool frequency of the PD patient group was lower than that of the healthy subject group.

(2) Biochemical Test

FIG. 1 shows a correlation between the serum LBP level and the stool frequency (A: PD group, B: Control group). In the PD patient group, a positive correlation was observed between the serum LBP level and the stool frequency, but this correlation was not observed in the healthy subject group (FIG. 1A and FIG. 1B). It is inferred from these results that a lower serum LBP level leads to worse deterioration of the PD condition. Accordingly, it is possible to determine deterioration of the disease condition of a PD patient by monitoring the blood LBP level in a single PD patient.

(3) Change in PD Pathological Condition in 2 Years

PD patients were divided into two groups for comparison, a group (worsening group) in which the deterioration of the PD condition is large and a group (non-worsening group) of those other than the worsening group, using the change in the condition after 2 years relative to that at the start of observation (0 year) as an indicator. Patients who were worsened by 15 points or more in the total of UPDRS or who were admitted or could not attend a hospital due to deterioration of the PD condition were identified in the worsening group. Patients who were worsened by less than 15 points in the total score of UPDRS were identified in the non-worsening group.

(3-1) Comparison of Scores of Worsening Group and Non-Worsening Group

Table 4 shows the comparison of scores when the patients were divided into a worsening group and a non-worsening group.

TABLE 4

| | Comparison of patient background | | | |
|---|---|---|---|---|
| | At the start of observation (0 year) | | After 2 years | |
| | Worsening group (n = 18) | Non-worsening group (n = 18) | Worsening group (n = 18) | Non-worsening group (n = 18) |
| Age (year) | 70.2 ± 5.6 | 67.0 ± 8.2 | | |
| Sex (actual number, %) | | | | |
| Male | 10 (52.6%) | 4 (22.2%) | | |
| Female | 8 (42.1%) | 14 (77.8%) | | |
| Disease duration (year) | 9.2 ± 4.6 | 9.8 ± 6.1 | | |
| B M I (kg/m$^2$) | 20.4 ± 2.7 | 19.6 ± 2.4 | 21.7 ± 2.5 | 19.4 ± 2.6 |
| UPDRS Part 1 score | 3.17 ± 2.4 | 2.4 ± 1.9 | 5.1 ± 3.8 | 1.9 ± 1.9 |
| UPDRS Part 2 score | 12.3 ± 7.2 | 9.4 ± 5.7 | 21.8 ± 8.5 | 11.9 ± 6.4 |
| UPDRS Part 3 score | 28.9 ± 13.5 | 21.6 ± 8.1 | 36.5 ± 15.9 | 20.2 ± 8.1 |
| UPDRS Part 4 score | 3.5 ± 2.0 | 2.9 ± 2.8 | 6.3 ± 3.9 | 4.6 ± 2.6 |
| UPDRS total score | 51.4 ± 24.9 | 36.3 ± 13.2 | 70.3 ± 27.1 | 38.6 ± 14.2 |
| L-dopa equivalent dose | 449 ± 174 | 390 ± 186 | 465.6 ± 206 | 497 ± 202 |

(3-2) Change in Clinical Parameter in 2 Years

Table 5 shows the changes in serum LBP level by comparison of those at the start of observation and at the time point after 2 years.

TABLE 5

Change in serum LBP level after 2 years

| | | 0 year | After 2 years |
|---|---|---|---|
| LBP level (ng/ml) | Worsening group | 12890 ± 3614 | 12449 ± 3433 |
| | Non-worsening group | 11925 ± 3298 | 12545 ± 3597 |

Table 5 demonstrates that the serum LBP level in the worsening group decreases after 2 years, but the serum LBP level in the non-worsening group rather tends to increase.

Figure 2:
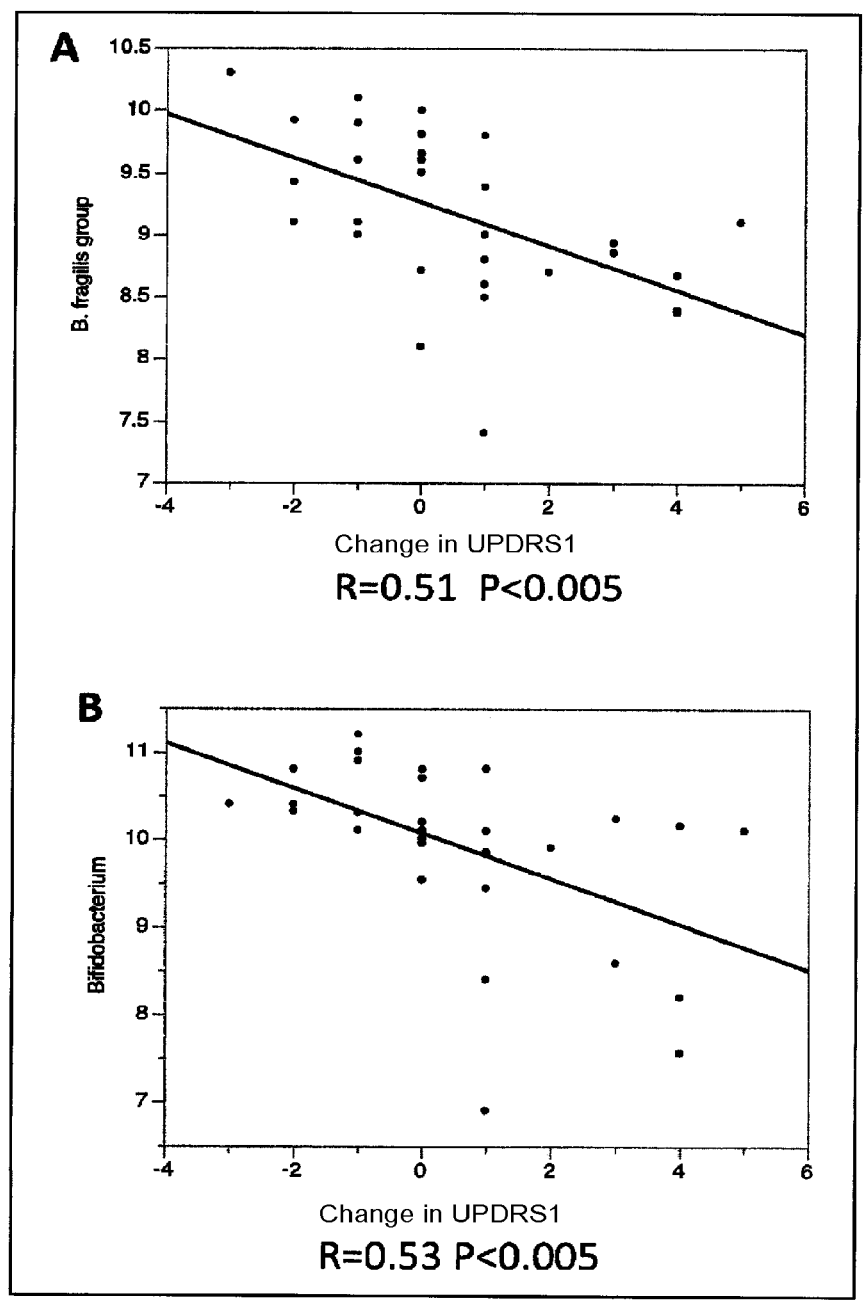
FIG. 2 shows a correlation between the change in the UPDRS Part 1 score (the change two years after the start of observation) and the number of *Bacteroides fragilis* group (A) or *Bifidobacterium* (B) at the start of observation.

(4) Correlation Between Change in Clinical Symptom of PD and Change in Bacterial Composition Correlation of the amount of change in the score (the amount of change two years after the start of observation) of the UPDRS Part 1 (mentation, behavior, and mood) score as the clinical symptom of PD with the bacterial number of *Bacteroides fragilis* group or *Bifidobacterium* at the start of observation (0 year) was examined. The results are shown in FIG. 2. A significant negative correlation with the amount of change of the score of UPDRS Part 1 after 2 years was observed (FIGS. 2A and 2B). From the results, it is considered that the bacterial numbers of *Bifidobacterium* and *Bacteroides fragilis* group at the start of observation (0 year) can be used as a marker for determination of a risk of deterioration of PD (in particular, psychiatric symptom).

Figure 3:
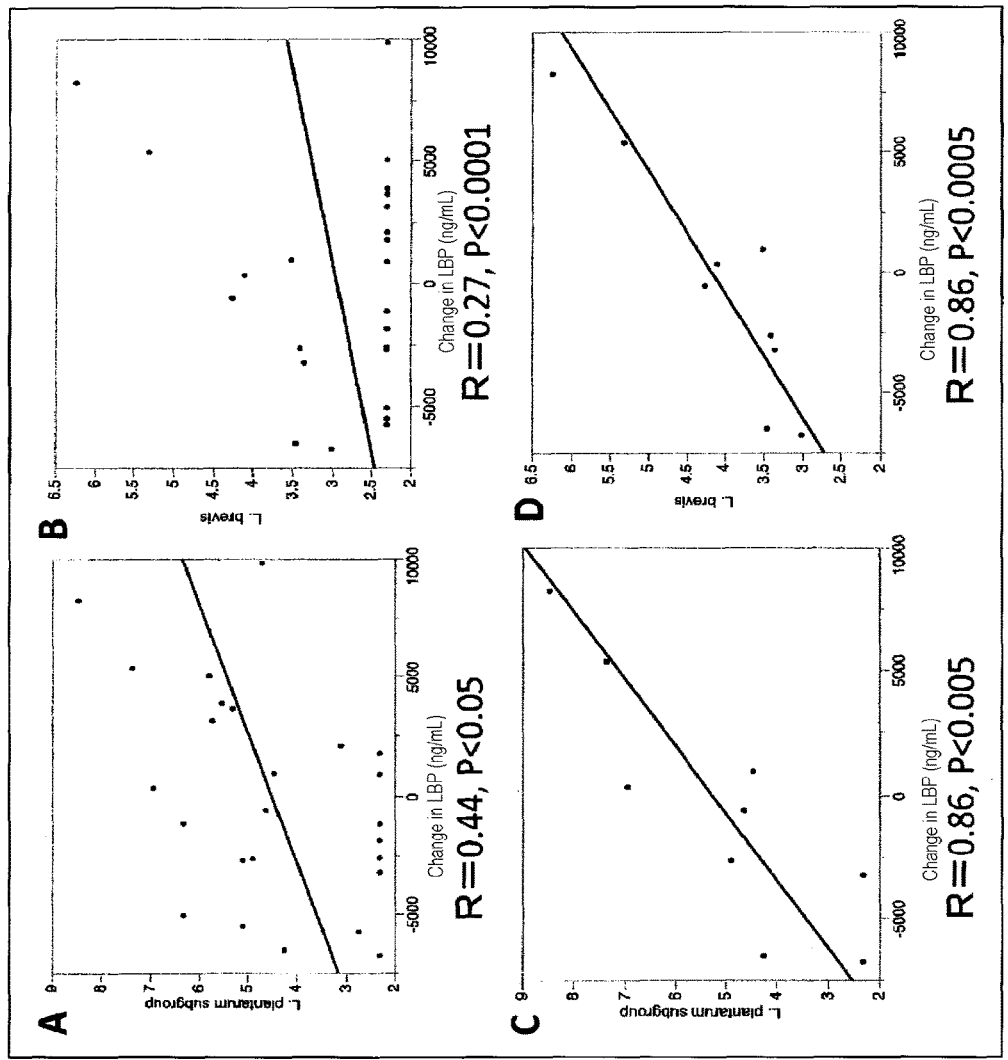
FIG. 3 shows a correlation between the change in the serum LBP level (the change two years after the start of observation) and the number of *Lactobacillus plantarum* subgroup (A) or *Lactobacillus brevis* (B) at the start of observation. The graph (C) shows the correlation obtained by excluding samples in which the number of *Lactobacillus plantarum* subgroup is below the detection limit, and the graph (D) shows the correlation obtained by excluding samples in which the number of *Lactobacillus brevis* is below the detection limit.

(5) Correlation Between Change in Serum LBP Level and Change in Bacterial Composition FIG. 3 shows the results of examination of the correlation between the change in the serum LBP level (the change two years after the start of observation) and the bacterial number of *Lactobacillus brevis* or *Lactobacillus plantarum* subgroup at the start of observation (0 year). The change in the serum LBP level showed a significant positive correlation with the bacterial numbers of *Lactobacillus plantarum* subgroup and *Lactobacillus brevis* at the start of observation (0 year) (FIG. 3A and FIG. 3B). Strong correlations were observed in the groups in which samples below the detection limit of *Lactobacillus plantarum* subgroup or *Lactobacillus brevis* were excluded (FIG. 3C and FIG. 3D). These results suggest that a larger bacterial number of *Lactobacillus brevis* at the start of observation (0 year) or a larger bacterial number of *Lactobacillus plantarum* subgroup at the start of observation (0 year) leads to a higher serum LBP level later (the condition of PD will become better) and that in contrast, a smaller bacterial number of *Lactobacillus brevis* at the start of observation (0 year) or a smaller bacterial number of *Lactobacillus plantarum* subgroup at the start of observation (0 year) leads to a lower serum LBP level later (the condition of PD will become severe). Since a change in the serum LBP level probably has a significant positive correlation with the bacterial numbers of *Lactobacillus brevis* and *Lactobacillus plantarum* subgroup at the start of observation (0 year), it is considered that the numbers of these bacteria at the start of observation (0 year) can be used as a marker for determination of a risk of deterioration of PD.

Figure 4:
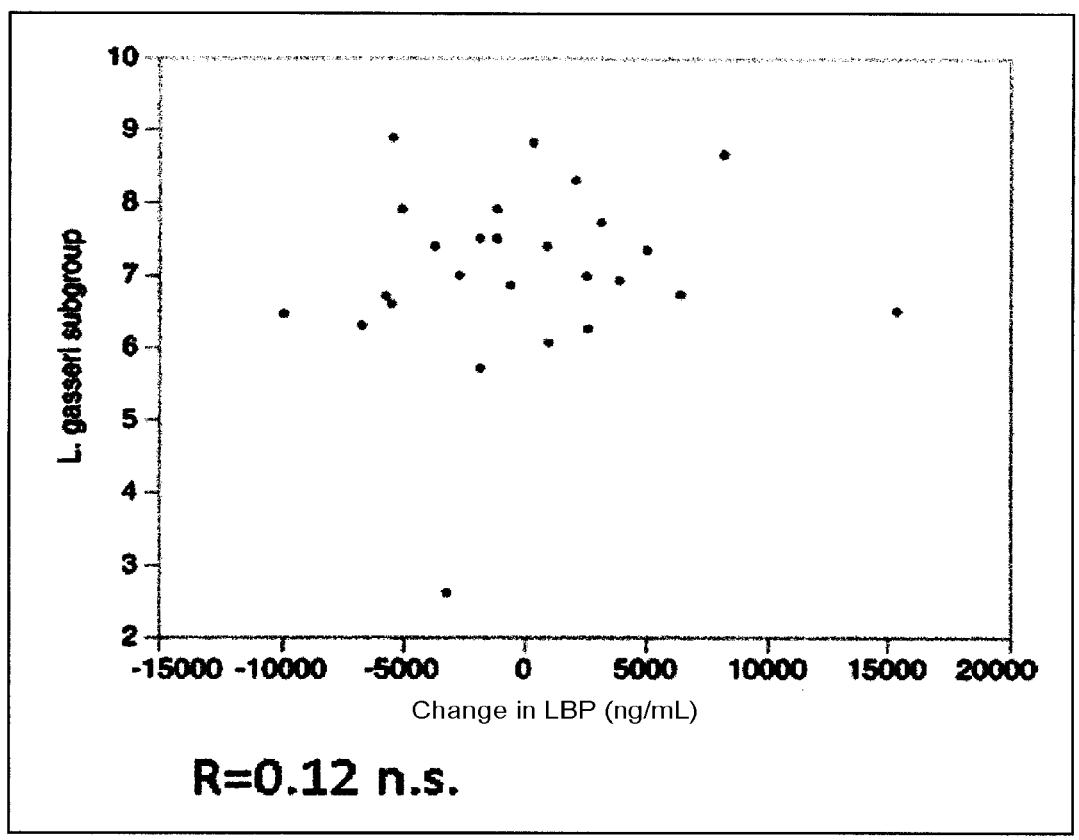
FIG. 4 shows a correlation between the change in the serum LBP level (the change two years after the start of observation) and the number of *Lactobacillus gasseri* subgroup at the start of observation.

FIG. 4 shows the results of verification of the correlation between the change in the serum LBP level (the change two years after the start of observation) and the number of *Lactobacillus gasseri* subgroup at the start of observation (0 year). Unlike the bacteria (intestinal bacteria of the present invention) shown in FIG. 3, there was no significant correlation between the change in the serum LBP level and *Lactobacillus gasseri* subgroup. As a result of analysis performed by the present inventors for various intestinal bacteria, it was shown that other intestinal bacteria (15 species) including *Lactobacillus gasseri* subgroup have no significant correlation with deterioration of Parkinson's disease (in particular, a risk of deterioration). Accordingly, it was confirmed that these intestinal bacteria cannot be used as a marker for determination of the present invention.

Figure 5:
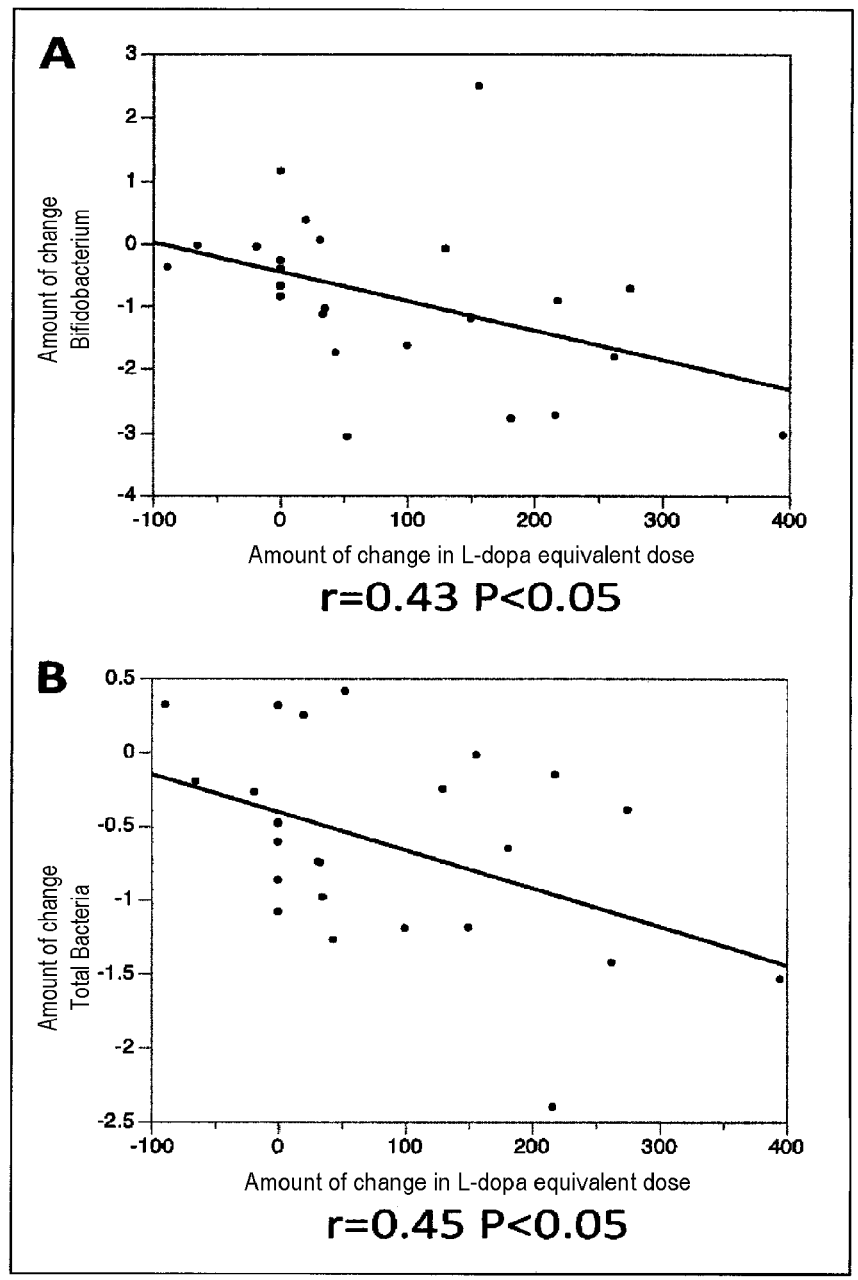
FIG. 5 shows a correlation between the amount of change in LED (L-dopa equivalent dose) and the amount of change in the number of *Bifidobacterium* (A) or the amount of change in the total number of intestinal bacteria in whole feces (B).

(6) Correlation Between Change in L-Dopa Equivalent Dose and Change in Bacterial Number FIG. 5 shows a correlation between the change in L-dopa equivalent dose (the amount of change two years after the start of observation) and the number of *Bifidobacterium* (A) or the total number of intestinal bacteria (B). The total number of intestinal bacteria was determined as the sum of the bacterial numbers of 19 bacterial species shown in Table 1. The number of *Bifidobacterium* (A) and the total number of intestinal bacteria (B) were decreased by an increase of L-dopa equivalent dose (LED), which L-dopa is a PD therapeutic agent, to show a significant negative correlation. There is a possibility that patients showing a larger decrease of *Bifidobacterium* consequently tend to cause deterioration of the symptom and need administration of a larger amount of medicine. From the results it is considered that the number of *Bifidobacterium* (amount of change) can be used as a marker for determination of a risk of deterioration of PD.

(7) Correlation Between Change in UPDRS and Change in Bacterial Number

Figure 6:
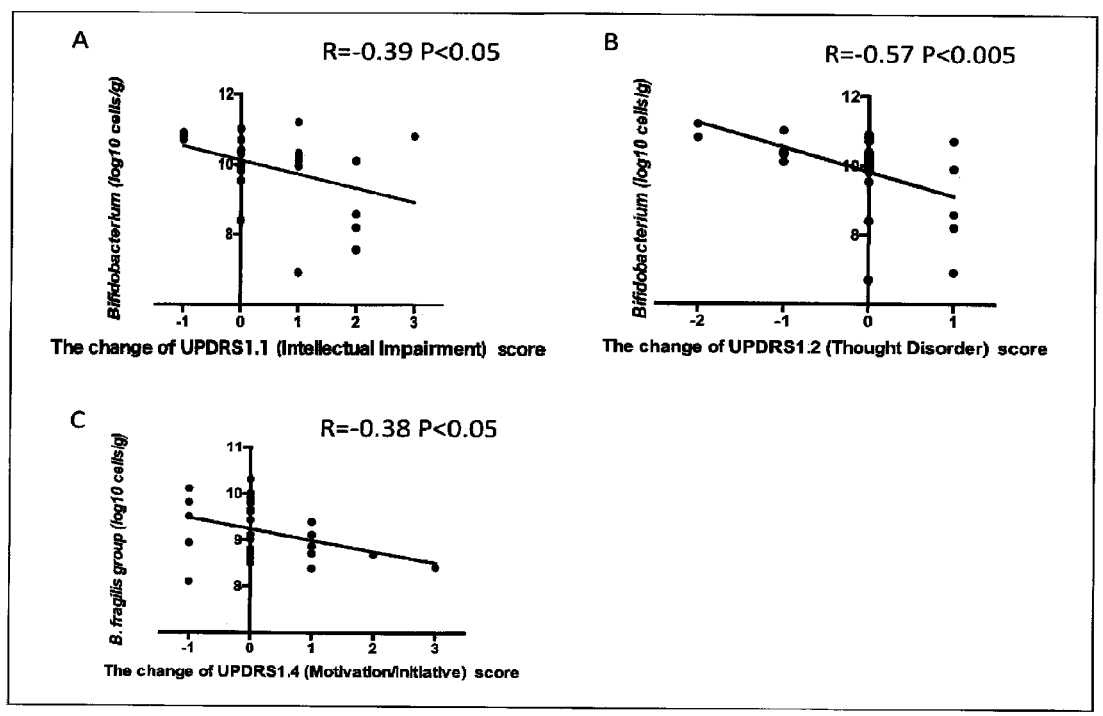
FIG. 6 shows (A) a correlation between the change in intellectual impairment score (UPDRS 1.1) (the change two years after the start of observation) and the number of *Bifidobacterium* at the start of observation, (B) a correlation between the change in thought disorder score (UPDRS 1.2) (the change two years after the start of observation) and the number of *Bifidobacterium* at the start of observation, and (C) a correlation between the change in motivation/initiative score (UPDRS 1.4) (the change two years after the start of observation) and the number of *Bacteroides fragilis* group at the start of observation.

FIG. 6 shows a correlation between the change of a subscale of a PD unification scale, UPDRS, (the amount of change two years after the start of observation) and the bacterial number at the start of observation. Among sub-items of UPDRS Part 1 (mentation, behavior, and mood), 1.1 (intellectual impairment), 1.2 (thought disorder), and 1.4 (motivation/initiative) were examined. As a result, negative correlations were shown between *Bifidobacterium and the change in* 1.1 (intellectual impairment) or 1.2 (thought disorder) score (FIGS. 6A and 6B) and between *Bacteroides fragilis* group and the change in 1.4 (motivation/initiative) score (FIG. 6C). This means that deterioration of PD condition can be determined by measuring the numbers of these bacteria.

As described above, intestinal bacteria can be used for determination of progress of the pathological condition of PD.

The invention claimed is:

1. A method for detecting deterioration of a disease condition of a patient having a Parkinson's disease, the method comprising:

obtaining samples from the patient comprising at least one intestinal bacterium selected from the group consisting of *Bifidobacterium, Bacteroides fragilis* group, *Lactobacillus brevis*, and *Lactobacillus plantarum* subgroup at two or more different time points, measuring the number of the at least one intestinal bacterium or the total numbers of the intestinal bacteria in the samples of the patient and comparing the numbers between the samples, wherein the measuring comprises culturing the at least one intestinal bacterium or the intestinal bacteria in a medium and counting the number of the at least one intestinal bacterium or the intestinal bacteria; culturing the at least one intestinal bacterium or the intestinal bacteria in a medium and measuring turbidity or absorbance of the culture; using a FISH method; using a quantitative RT-PCR method; or a combination thereof, and determining that the disease condition of the patient is getting severe when the number of the at least one intestinal bacterium or the intestinal bacteria is decreased over time or determining that the disease condition of the patient is getting mild when the number of the at least one intestinal bacterium or the intestinal bacteria is increased over time; or determining that the disease condition of the patient is getting severe when an amount of change in the number of the at least one intestinal bacterium or the intestinal bacteria over time is smaller than a reference or determining that the disease condition of the patient is getting mild when the amount of change in the number of the at least one intestinal bacterium or the intestinal bacteria over time is greater than the reference, wherein the reference is a value Q of a vertical axis at the time point of 0 in a horizontal axis in an approximate line equation created in advance for a correlation between the amount of change in the number of the at least one intestinal bacterium or the number of the intestinal bacteria measured at two or more different time points in the vertical axis and the deterioration of the disease condition in the horizontal axis of Parkinson's disease patients, wherein the measuring is conducted by using a quantitative RT-PCR method comprising:

extracting RNA from the samples, synthesizing cDNA by a reverse transcription (RT) reaction using a nucleic acid fragment or primer that hybridizes to extracted RNA and subsequently performing a PCR using the cDNA as a template, and detecting a DNA fragment amplified by the PCR, wherein the PCR is performed using at least one primer set selected from the group consisting of:

a primer set comprising a primer comprising the nucleotide sequence of SEQ ID NO: 5 and a primer comprising the nucleotide sequence of SEQ ID NO: 6;

a primer set comprising a primer comprising the nucleotide sequence of SEQ ID NO: 7 and a primer comprising the nucleotide sequence of SEO ID NO: 8;

a primer set comprising a primer comprising the nucleotide sequence of SEQ ID NO: 21 and a primer comprising the nucleotide sequence of SEQ ID NO: 22;

a primer set comprising a primer comprising the nucleotide sequence of SEQ ID NO: 29 and a primer comprising the nucleotide sequence of SEQ ID NO: 30; and a primer set comprising primers comprising the nucleotide sequences of SEO ID NOs: 1 to 38.

2. The method according to claim 1, wherein the deterioration of the disease condition of a Parkinson's disease patient is deterioration of a constipation symptom or a psychiatric symptom.

3. The method according to claim 2, wherein the psychiatric symptom is at least one selected from the group consisting of hallucination, cognition, and motivation.

4. The method according to claim 1, wherein the quantitative RT-PCR method further comprises observing an amplified PCR product over time and identifying the number of PCR cycles at the time when an amount of the PCR product reaches a predetermine level, wherein the observing of the amplified PCR product over time is performed by labeling the PCR product with an intercalating fluorescent dye, and measuring a fluorescence intensity at each PCR cycle.

5. The method according to claim 1, wherein the quantitative RT-PCR method further comprises preparing a calibration curve for use in RT-PCR, wherein the calibration curve is used in the quantification of the at least one intestinal bacterium in the sample, wherein the calibration curve is prepared by plotting the numbers of each of the intestinal bacterium measured by a DAPI method on a horizontal axis and $C_T$ values corresponding to the numbers obtained by RT-PCR on a vertical axis.

6. The method according to claim 1, wherein the samples are from feces of the patient and wherein the determining comprises determining that the disease condition of the patient is getting severe when an amount of change in the total number of the intestinal bacteria per 1 g sample over time is smaller than of a reference or determining that the disease condition of the patient is getting mild when the amount of change in the total number of the intestinal bacteria per 1 g sample over time is greater than of the reference, wherein the reference is a value $Q_1$ of a vertical axis at the time point of 0 in a horizontal axis in an approximate line equation of a correlation graph between an amount of change in L-dopa equivalent dose set on the horizontal axis and an amount of change in the total number of intestinal bacteria in w % bole feces set on the vertical axis.

7. The method according to claim 1, wherein the samples are samples from feces of the patient and wherein the determining comprises determining that the disease condition of the patient is getting severe when an amount of change in the number of *Bifidobacterium* per 1 g sample over time is smaller than a reference or determining that the disease condition of the patient is getting mild when the amount of change in the number of the *Bifidobacterium* per 1 g sample over time is greater than the reference, wherein the reference is a value $Q_2$ of a vertical axis at the time point of 0 in a horizontal axis in an approximate line equation of a correlation graph between an amount of change in L-dopa equivalent dose set on the horizontal axis and an amount of change in the number of *Bifidobacterium* set on the vertical axis.

* * * * *